(12) United States Patent
Hoeg et al.

(10) Patent No.: US 7,967,742 B2
(45) Date of Patent: Jun. 28, 2011

(54) METHOD FOR USING VARIABLE DIRECTION OF VIEW ENDOSCOPY IN CONJUNCTION WITH IMAGE GUIDED SURGICAL SYSTEMS

(75) Inventors: Hans David Hoeg, Arcadia, CA (US); Nathan Jon Schara, Pasadena, CA (US); Eric Lawrence Hale, Altadena, CA (US)

(73) Assignee: Karl Storz Imaging, Inc., Goleta, CA (US)

( * ) Notice: Subject to any disclaimer, the term of this patent is extended or adjusted under 35 U.S.C. 154(b) by 1813 days.

(21) Appl. No.: 11/058,311

(22) Filed: Feb. 14, 2005

(65) Prior Publication Data

US 2006/0189842 A1    Aug. 24, 2006

(51) Int. Cl.
*A61B 1/00* (2006.01)
*A61B 1/04* (2006.01)
*A61B 1/06* (2006.01)

(52) U.S. Cl. .................. 600/103; 600/117; 600/173

(58) Field of Classification Search .............. 600/103, 600/109, 117–118, 160, 173
See application file for complete search history.

(56) References Cited

U.S. PATENT DOCUMENTS

| | | | |
|---|---|---|---|
| 3,572,325 A | 3/1971 | Bazell et al. ............... 128/6 |
| 3,880,148 A | 4/1975 | Kanehira et al. ............ 128/6 |
| 4,697,577 A | 10/1987 | Forkner ....................... 128/6 |
| 5,230,623 A | 7/1993 | Guthrie et al. .............. 433/72 |
| 5,313,306 A | 5/1994 | Kuban et al. ............... 348/65 |
| 5,531,227 A | 7/1996 | Schneider ............... 128/653.1 |
| 5,617,857 A | 4/1997 | Chader et al. ........... 128/653.1 |
| 5,623,560 A | 4/1997 | Nakajima et al. ........... 382/295 |
| 5,638,819 A * | 6/1997 | Manwaring et al. ......... 600/424 |
| 5,661,519 A | 8/1997 | Franetzki .................... 348/66 |
| 5,677,763 A | 10/1997 | Redmond .................... 356/73 |
| 5,704,897 A * | 1/1998 | Truppe ....................... 600/117 |
| 5,899,851 A | 5/1999 | Koninckx ................... 600/117 |
| 5,920,395 A | 7/1999 | Schulz ....................... 356/375 |
| 5,954,634 A | 9/1999 | Igarashi ..................... 600/109 |
| 5,976,076 A | 11/1999 | Kolff et al. ................. 600/166 |
| 6,007,484 A | 12/1999 | Thompson .................. 600/173 |
| 6,097,423 A | 8/2000 | Mattsson-Boze et al. ...... 348/65 |
| 6,167,296 A * | 12/2000 | Shahidi ...................... 600/427 |
| 6,241,657 B1 * | 6/2001 | Chen et al. .................. 600/117 |
| 6,371,909 B1 | 4/2002 | Hoeg et al. ................. 600/173 |
| 6,442,417 B1 | 8/2002 | Shahidi et al. .............. 600/429 |
| 6,464,631 B1 | 10/2002 | Girke et al. ................. 600/109 |
| 6,471,637 B1 | 10/2002 | Green et al. ................ 600/109 |
| 6,500,115 B2 | 12/2002 | Krattiger et al. ............ 600/173 |
| 6,505,065 B1 * | 1/2003 | Yanof et al. ................. 600/427 |
| 6,648,817 B2 | 11/2003 | Schara et al. ............... 600/173 |
| 6,663,559 B2 | 12/2003 | Hale et al. .................. 600/118 |
| 6,695,774 B2 | 2/2004 | Hale et al. .................. 600/173 |
| 2002/0007108 A1 * | 1/2002 | Chen et al. .................. 600/117 |
| 2002/0010384 A1 * | 1/2002 | Shahidi et al. .............. 600/118 |

(Continued)

FOREIGN PATENT DOCUMENTS

DE    299 07 430    10/1999

(Continued)

*Primary Examiner* — Philip R Smith
(74) *Attorney, Agent, or Firm* — St. Onge Steward Johnston & Reens LLC

(57) ABSTRACT

A method for a variable direction of view endoscope used in combination with an image guided surgical system to provide new diagnostic and surgical capabilities. The method provides the following capabilities: greatly improved endoscopic orientation capabilities, global monitoring of endoscopic viewing direction, and greatly improved surgical approach and procedure planning.

10 Claims, 10 Drawing Sheets

U.S. PATENT DOCUMENTS

| | | | |
|---|---|---|---|
| 2002/0045855 A1 | 4/2002 | Frassica | 604/109 |
| 2002/0099263 A1 | 7/2002 | Hale et al. | 600/117 |
| 2002/0161280 A1 | 10/2002 | Chatenever et al. | 600/112 |
| 2003/0016883 A1 | 1/2003 | Baron | 382/289 |
| 2003/0216639 A1* | 11/2003 | Gilboa et al. | 600/424 |
| 2004/0127769 A1 | 7/2004 | Hale et al. | 600/173 |
| 2004/0210105 A1 | 10/2004 | Hale et al. | 600/101 |
| 2005/0020878 A1* | 1/2005 | Ohnishi et al. | 600/117 |
| 2005/0020883 A1 | 1/2005 | Chatenever et al. | 600/173 |
| 2005/0027167 A1 | 2/2005 | Chatenever et al. | 600/173 |
| 2005/0033117 A1* | 2/2005 | Ozaki et al. | 600/109 |
| 2005/0054895 A1 | 3/2005 | Hoeg et al. | 600/117 |
| 2005/0113643 A1 | 5/2005 | Hale et al. | 600/118 |
| 2005/0154260 A1 | 7/2005 | Schara et al. | 600/173 |
| 2005/0187432 A1 | 8/2005 | Hale et al. | 600/117 |
| 2005/0228230 A1 | 10/2005 | Schara et al. | 600/171 |

FOREIGN PATENT DOCUMENTS

| | | |
|---|---|---|
| JP | 6269403 | 9/1994 |
| WO | WO 95/01749 | 1/1995 |
| WO | WO 01/22865 | 4/2001 |

* cited by examiner

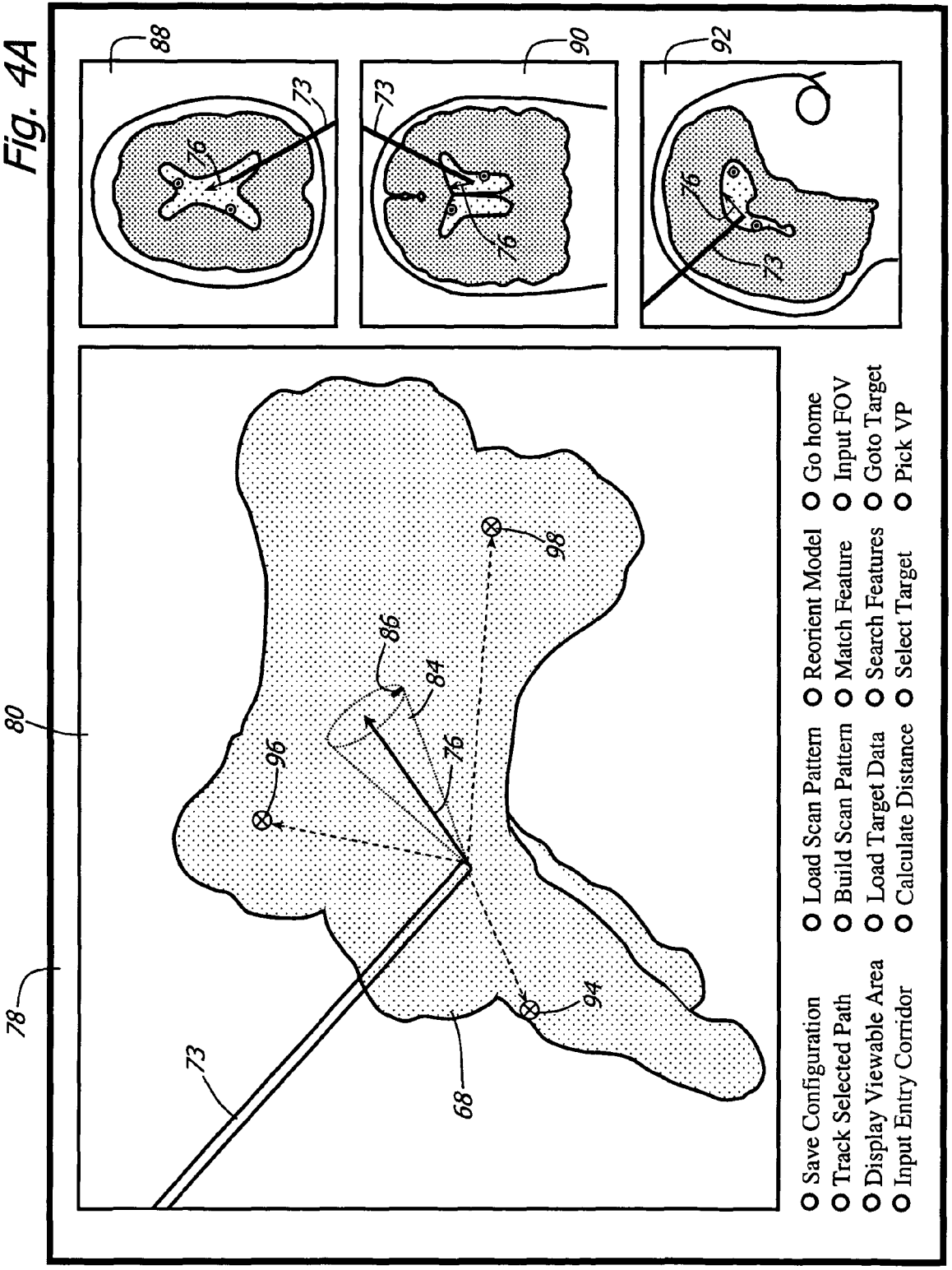

METHOD FOR USING VARIABLE DIRECTION OF VIEW ENDOSCOPY IN CONJUNCTION WITH IMAGE GUIDED SURGICAL SYSTEMS

FIELD OF THE INVENTION

The present invention relates to endoscopic surgical navigation by the combination of variable direction of view endoscopy and image guided surgery techniques, especially as it relates to neurosurgery.

BACKGROUND OF THE INVENTION

Image guided surgical navigation is the process of planning minimally invasive surgical approaches and guiding surgical tools towards targets inside a patient's body with the help of anatomical imaging information obtained with techniques such as ultrasound, magnetic resonance, and various radiographic techniques. Such anatomical imaging information is useful because during a minimally invasive procedure, the surgical tools and the subcutaneous anatomy are not directly visible to the surgeon. With early image guided surgical techniques, the surgeon had to rely on her ability to accurately correlate two-dimensional slice-plane data with the three dimensionality of the patient in order to safely guide tools in the surgical field. The main drawbacks with this method were that it required abstract visualization by the surgeon in an attempt to develop an accurate mental picture of the interior anatomy, and that it did not provide feedback to the surgeon about the position of the surgical instruments during a procedure. These problems were addressed with the advent of frameless stereotactic systems, as disclosed in U.S. Pat. No. 5,230,623 to Guthrie (1993), U.S. Pat. No. 5,531,227 to Schneider (1996), U.S. Pat. No. 5,617,857 to Chader (1997), and U.S. Pat. No. 5,920,395 to Schulz which could locate and display the real time global position of a surgical instrument relative to reconstructed computer graphical models of diagnostic imaging data obtained through newer techniques such as computed tomography, magnetic resonance imaging, positron emission tomography, ultrasound scans, and other techniques. The methods of frameless stereotaxy were further improved by methods which could provide real time virtual anatomical views from the viewpoint of the surgical instrument as it was positioned inside the patient, as disclosed in U.S. Pat. No. 6,167,296 (2000) and U.S. Pat. No. 6,442,417 (2002) to Shahidi.

The backbone of minimally invasive surgical procedures is the endoscope, which affords surgeons an actual view of the internal anatomy. The combination of endoscopy and image guided surgery is interesting because it brings together the interior view of the endoscope and the exterior perspective of the image guided surgical system, much like local visual information such as landmarks or street signs are correlated with a map or a global positioning system to accurately determine position in a landscape. This combination is suggested by Shahidi, who teaches correlating and overlaying real endoscopic images with virtual images of the same view reconstructed from global imaging data, affording advantages such as graphical image enhancement. Shahidi exclusively deals with images generated from the viewpoint of an endoscope or surgical instrument looking along its longitudinal axis, tying the disclosure to fixed-axis instruments. Disclosure U.S. Pat. No. 6,442,417 specifically teaches the use of virtual perspective images of regions outside the field of view of fixed-angle endoscope as substitutes for obtaining live endoscopic views of such regions. Variable direction of view endoscopes can provide real images of such areas without the need for much shaft movement or reinsertion of the endoscope from an alternate direction. Variable direction of view endoscopes, which can be either rigid or flexible, as disclosed in U.S. Pat. No. 3,880,148 to Kanehira (1975), U.S. Pat. No. 4,697,577 to Forkner (1987), U.S. Pat. No. 6,371,909 to Hoeg (2002), WIPO publication WO 01/22865A1 to Ramsbottom (2001), DE 29907430 to Schich (1999), U.S. Pat. No. 3,572,325 to Bazell et al. (1971), and U.S. Pat. No. 6,007,484 to Thompson (1999) typically have a mechanism at the tip allowing the user to change the viewing direction without moving the endoscope shaft. Electronic endoscopes, as disclosed in U.S. Pat. No. 5,954,634 to Igarashi (1998) and U.S. Pat. No. 5,313,306 to Kuban, et al. (1994), with extreme wide angle lenses that allow the user to selectively look at portions of the optical field also belong to the class of variable direction of view endoscopes.

The value of using image guidance system in conjunction with variable direction of view endoscopy is potentially much greater than for standard fixed-angle endoscopy. Firstly, such a combination would allow real and virtual image correlation over a much greater viewing range, which would mean improved approach planning, improved guidance capabilities, and improved procedures overall. Secondly, it would provide a significant betterment of viewing navigation with variable direction of view endoscopes. A problem introduced by variable direction of view endoscopes is that it is difficult for the surgeon to estimate the changing endoscopic line of sight, which has a variable relationship to the shaft axis, because the tip of the instrument is concealed during use. Getting an external estimate of where the endoscope is "looking" during a procedure is important as the surgeon tries to integrate preexisting knowledge of the anatomy with the viewing process. Even with indicator knobs and dials (as in United States patent application 20020099263), or markers along the imaging axis (U.S. Pat. No. 6,500,115 to Krattiger et al.) it can be difficult to estimate which part of the anatomy is being seen through the endoscope because the user does not know the location of endoscope tip, which is the point of origin for the variable view vector. Fixed-angle endoscopes do not suffer from this problem to the same degree because the viewing direction has a fixed relationship to the endoscope shaft and can often be mentally extrapolated by the surgeon during a procedure.

The solution to this problem is to use an image guided system to provide the surgeon with a global perspective of the endoscope's viewing direction. In order to achieve this, it is not sufficient to simply monitor the position of the shaft of the endoscope as described in the prior art and done in current practice. The endoscopic viewing direction has to monitored as well. One way to do this, is to equip the view changing mechanism with an emitter/transponder which can be sensed through the patient's skin by external sensors. A better way to monitor the viewing direction is to sense its orientation relative to the endoscope shaft which position can be found by current image guided systems. This requires a variable direction endoscope instrumented with means to monitor its internal configuration. By combining the instrument's internal configuration data with its global position data as determined by the image guided surgical system, its viewing direction can then be determined. The variable direction of view endoscopes disclosed in the prior art listed above, are not equipped with means of monitoring their internal configuration. Apparently the only system currently capable of such internal configuration monitoring is the system disclosed in U.S. Pat. No. 6,663,559 by Hale et al. which discloses a novel system and method for precision control of variable direction of view endoscopes, making it ideal for integration with an image guided surgical system.

With proper integration, the extended viewing capabilities of an appropriately instrumented variable direction of view endoscope such as the one disclosed by Hale, combined with the features of an image guided surgical system could simplify and improve surgical planning and procedure. Global view vector monitoring would solve many of the endoscopic orientation problems surgeons face during variable direction of view endoscopy. Further, such an omnidirectional viewing navigation system could greatly expand the graphical image enhancement techniques disclosed by Shahidi.

From the discussion above, it should become apparent that there is a need for a method which provides the following capabilities: improved endoscopic orientation capabilities, global monitoring of endoscopic position and viewing direction, and improved surgical approach and procedure planning.

BRIEF SUMMARY OF THE INVENTION

In accordance with the present invention, a method is provided for combining variable direction of view endoscopy system with image guided techniques yielding significantly improved viewing capabilities and novel surgical planning features. A method for improving a diagnostic or surgical procedure involving a variable direction of view endoscope with a variable line of sight comprising: acquiring volumetric scan data of a subsurface structure; positioning said endoscope relative to said subsurface structure; establishing the position of said endoscope relative to said subsurface structure; acquiring internal endoscope configuration data; displaying representations of said subsurface structure and said endoscopic line of sight in their correct relative spatial relationship based on said volumetric scan data, said endoscope position data, and said internal endoscope configuration data.

BRIEF DESCRIPTION OF THE DRAWINGS

FIGS. 4A and 4B shows a user interface for an omnidirectional viewing navigation system according to an embodiment of the present invention.

DETAILED DESCRIPTION OF THE INVENTION

The following detailed description illustrates the invention by way of example, not by way of limitation of the principles of the invention. This description will clearly enable one skilled in the art to make and use the invention, and describes several embodiments, adaptations, variations, alternatives and uses of the invention, including what we presently believe is the best mode of carrying out the invention.

Prior Art

Figure 1:
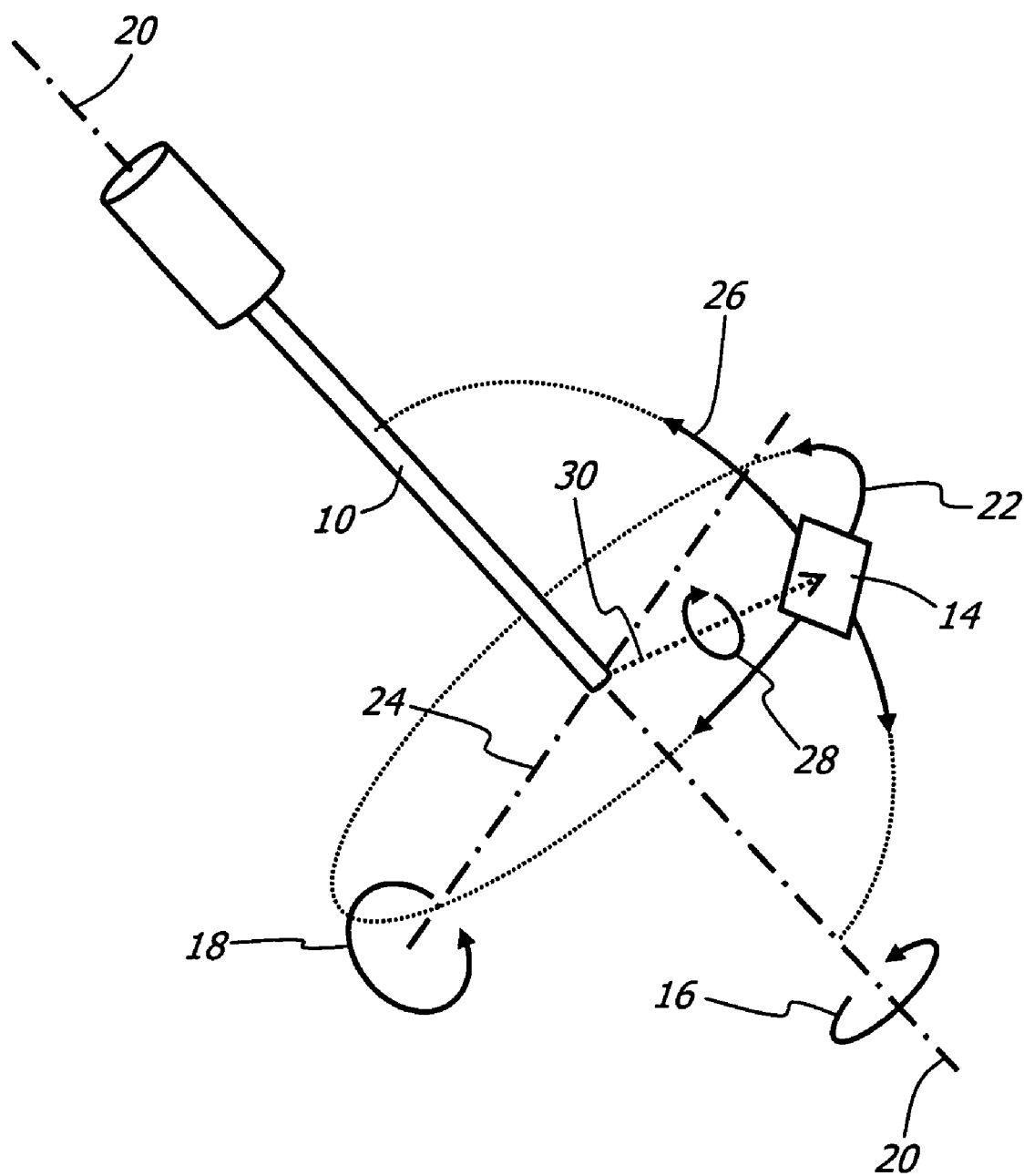
FIG. 1 shows the operating principle of a variable direction of view endoscope.

Referring now to the drawings, in which like reference numbers represent similar or identical structures throughout, FIG. 1 is a diagram of a basic variable direction of view endoscope 10. Such an endoscope 10 typically has a view vector 12, and a corresponding view field 14, with at least two degrees of freedom 16, 18. The $1^{st}$ degree of freedom 16 permits rotation of the view vector 12 about the longitudinal axis 20, which allows the view vector 12 to scan in a latitudinal direction 22. The $2^{nd}$ degree of freedom 18 permits rotation of the view vector 12 about an axis 24 perpendicular to the longitudinal axis 20, which allows the view vector 12 to scan in a longitudinal direction 26. A $3^{rd}$ degree of freedom 28 may also be available because it is usually possible to adjust the rotational orientation of the endoscopic image.

Figure 2:
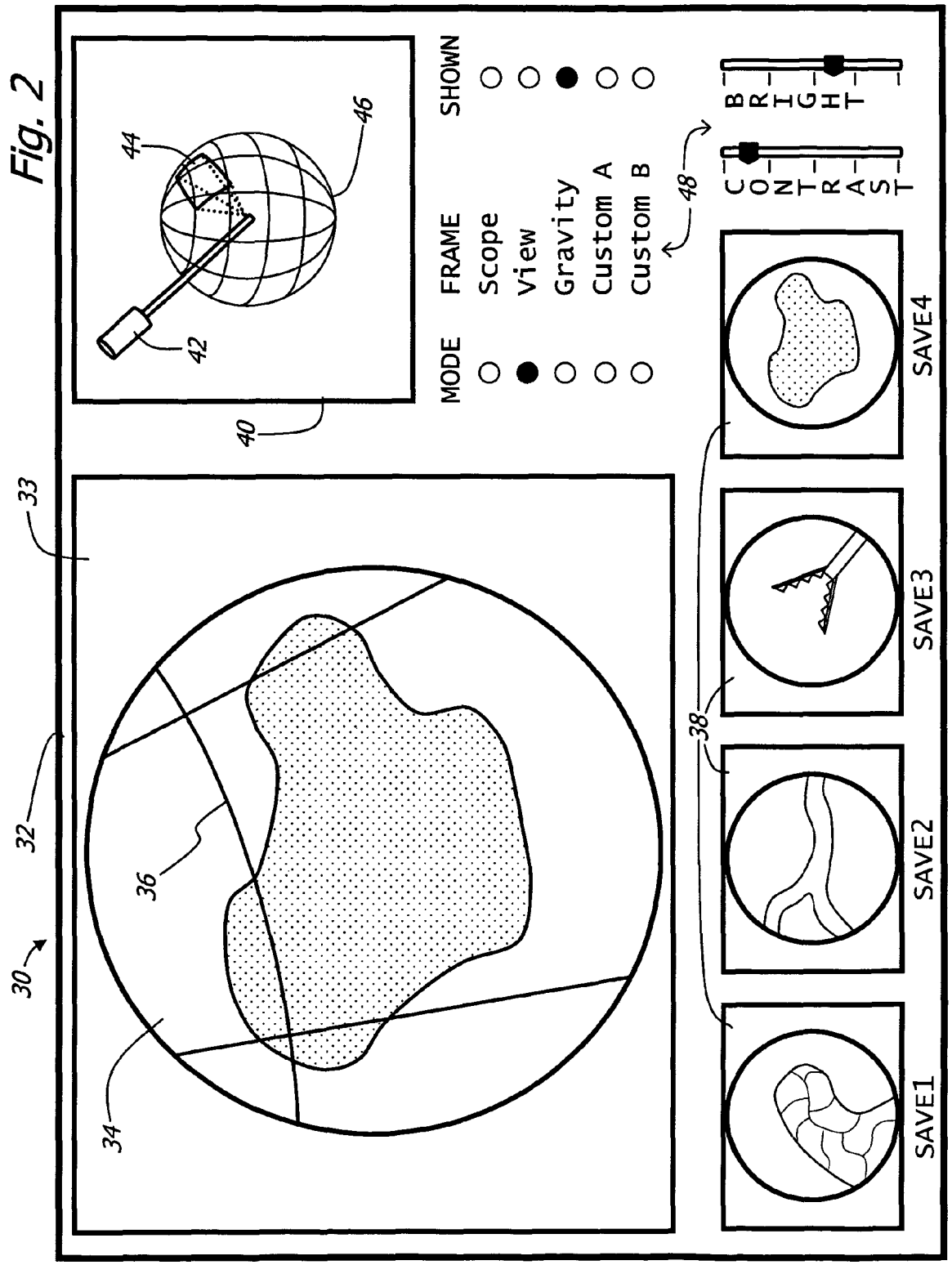
FIG. 2 shows the user interface for an omnidirectional endoscopic system according to an embodiment of the present invention.

FIG. 2 illustrates an embodiment of how the endoscopic video image and additional relevant information is presented to the user on a display device 30. The screen of the display device 32 is organized into multiple sections, each with a different purpose. A large section of the screen 33 is used to display an image 34 from the endoscope. A representation of a coordinate system 36 may be graphically superimposed on the image 34 to aid the user in viewing navigation. Several captured images 38 are displayed, each one corresponding to a previously saved endoscope configuration. Another section of the screen 40 provides a computer generated depiction of the endoscope 42 to assist the user in understanding the orientation of the current view 44 relative to the endoscope and relative to gravity or a user selected reference frame 46, which coincides with the coordinate system 36. The depiction 42 may include markings (not shown) to aid the user's spatial understanding. In yet another section of the screen, the current mode settings 48 are displayed.

Preferred Embodiment

Figure 3:
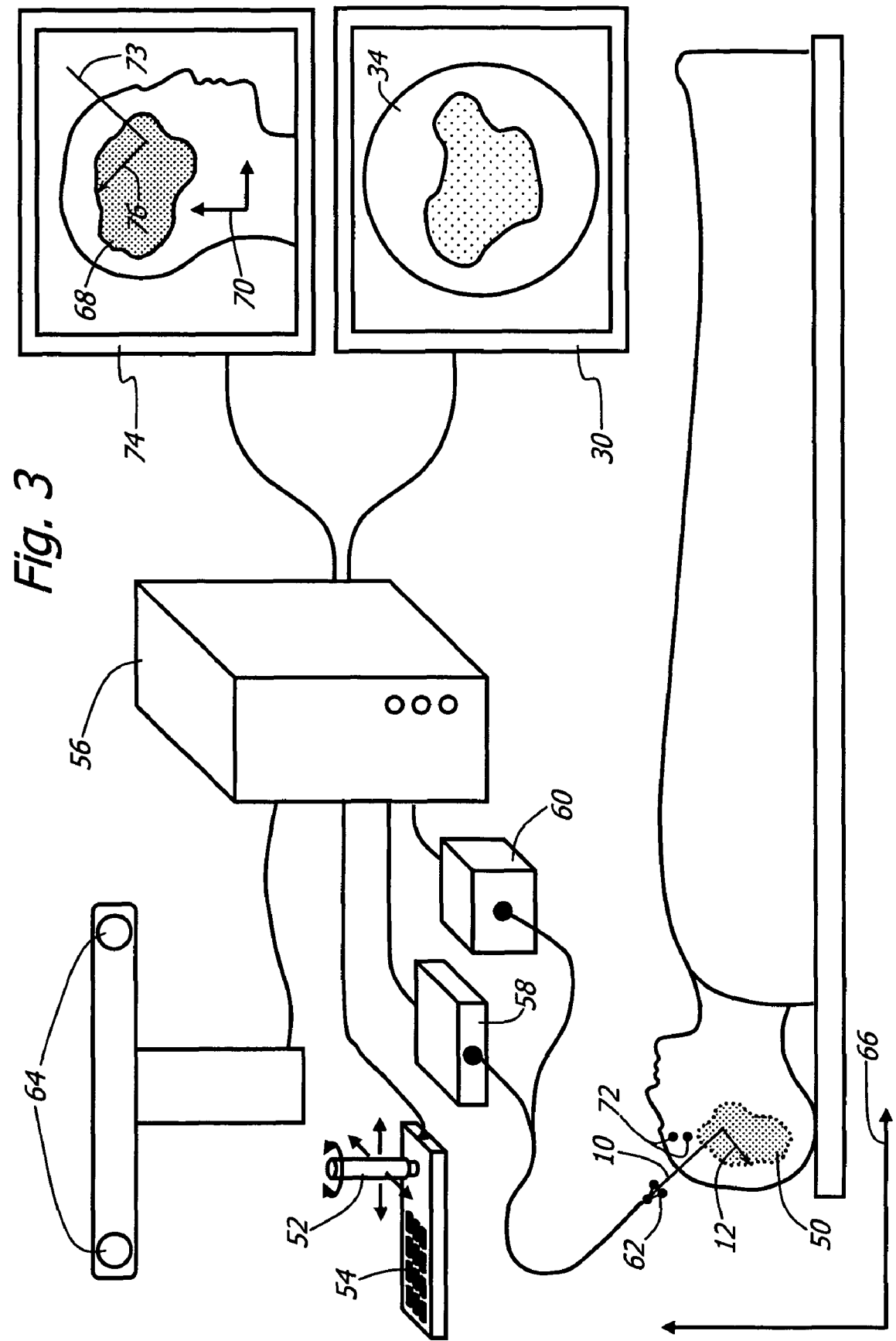
FIG. 3 shows an omnidirectional viewing navigation system according to the present invention.

FIG. 3 shows a variable direction of view endoscopic system integrated with an image guided surgical system. A rigid instrumented endoscope 10 with an adjustable view vector 12, is positioned with its distal end in an anatomical structure 50 (Illumination for the anatomical structure 50 is delivered through the endoscope 10 from a standard light source, not shown). The endoscope 10 is equipped with actuators and sensors (not shown) that enable precise electromechanical control of the view vector 12. The user controls the view vector 12 through an input device such as a joystick 52 or a keypad 54. A central control unit 56 processes the user input and information about the current endoscope configuration to calculate the appropriate adjustment of the view vector 12 without changing the position of the endoscope 10. The actuator control unit 58 controls the endoscope configuration while an image acquisition unit 60 receives image signals from the endoscope 10 and adjusts them as needed before relaying them to the central control unit 56. An endoscopic video image 34 and additional relevant information are sent to a display device 30. Light emitting diodes 62 (or other transponders) on the endoscope 10 are tracked by a set of cameras 64. The central control unit 56 uses signals from the cameras 64 to calculate the position of the endoscope 10 in a global reference frame 66. A computer graphical model 68 of the interior anatomical structure 50, reconstructed from volumetric scan data obtained from an imaging procedure, has a model reference frame 70. By correlating the model reference frame 70 with the global reference frame 66 with the help of features or fiducial markers 72 on the patient's body, the central control unit 56 can calculate and display a graphical representation 73 of the endoscope 10 to illustrate its position relative to the anatomical structure 50 represented by a graphical model 68 on another display device 74 (alternatively on the same monitor 30). The viewing direction 12 is represented graphically as a view vector 76. The central control unit 56 keeps track of the orientation of the view vector 76 and uses the signals from the two cameras 64 which sense the emitters 62 on the endoscope 10 to calculate and display the relative positions of the endoscope 10, the view vector 76, and the model 68.

Figure 4B:
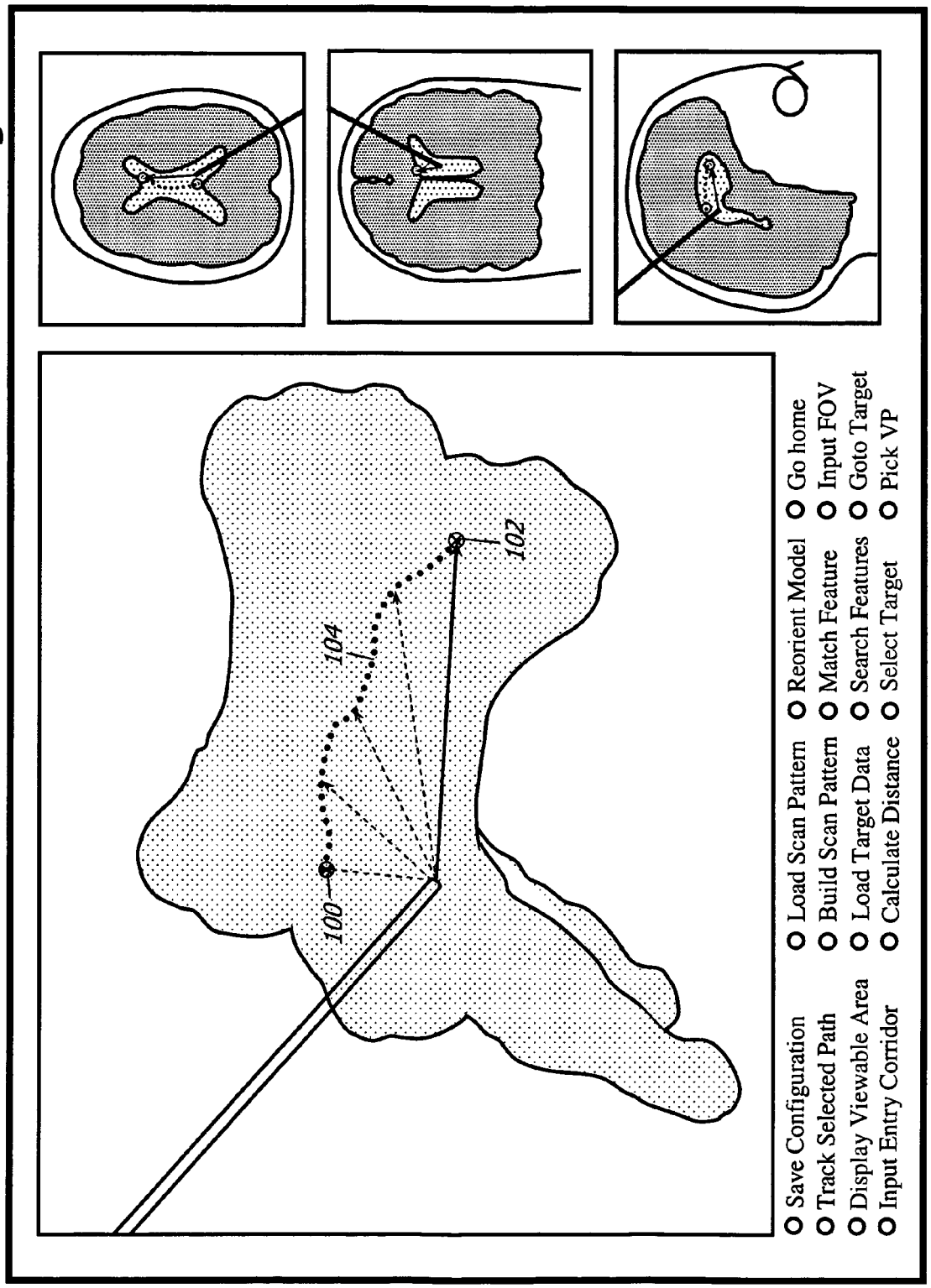
Figure 5A:
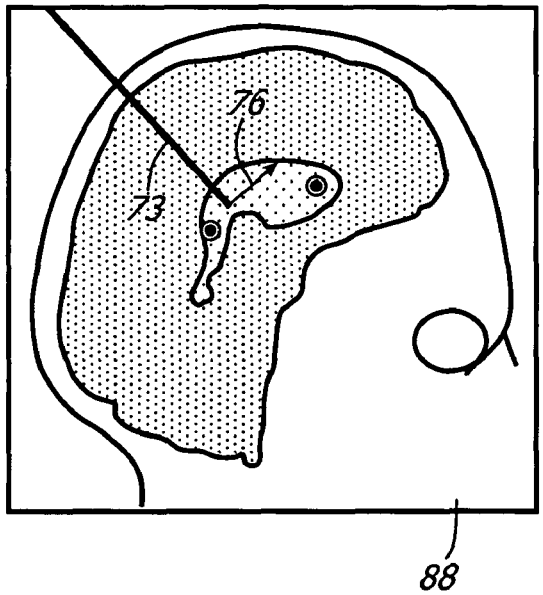
FIGS. 5A, 5B, and 5C shows graphical representations of the endoscopic viewing direction relative to reconstructed models of the coronal, axial, and sagital imaging planes, according to the present invention.
Figure 5B:
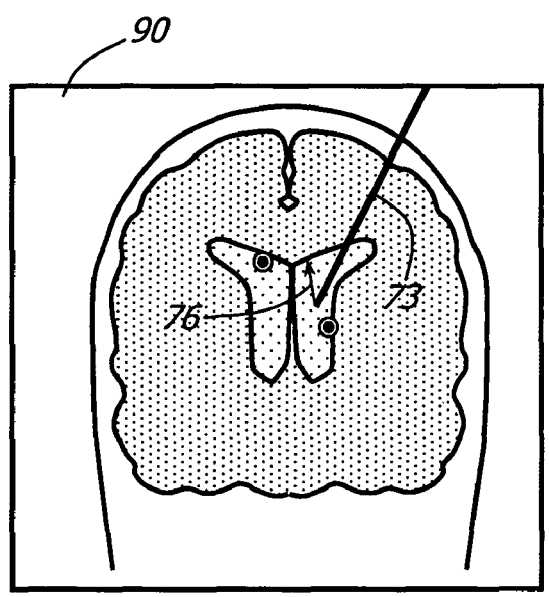
Figure 5C:
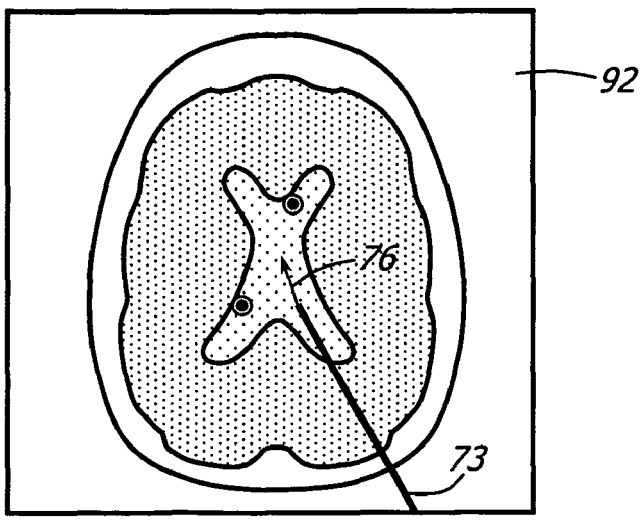

The relative positions of the endoscope, its viewing direction, the anatomy, and additional relevant information are presented to the user as shown in FIG. 4A (for simplicity many menu options included in a typical display for an image guided stereotactic system are not shown here). The screen of the display device 78 is organized into multiple sections which display information about the endoscopic diagnosis or surgical procedure. A section of the screen 80 is used to display the anatomical model 68 and graphical representations of the endoscope 73 and the view vector 76, respectively, giving a global perspective of the endoscopic viewing direction and the location of the features seen in the endoscopic image relative to the surrounding anatomy. To aid the user's spatial understanding, a representation of the endoscopic view cone 84 is also displayed, and the orientation of the endoscopic image is shown by a marker 86, indicating the up-direction of the image. Three other sections 88, 90, 92 show the orientation of the view vector 76 relative to the sagital, coronal, and axial slice planes containing the endoscope tip point. These slice planes, also shown in FIGS. 5A, 5B, and 5C, change as the tip location of the endoscope is moved. Memory positions 94, 96, 98 indicate saved viewing locations to which the user can return (see the captured images 38 in FIG. 2). These memory positions 94, 96, 98 are fixed in the global coordinate system, so the endoscope can always find them, regardless of whether the body of the endoscope has moved since these positions were saved. This memory feature is useful for showing the relative arrangement of features in the surgical space. It is also useful if the user wants to adjust the position of the endoscope while maintaining a fixed view. It is further possible to select specific points 100, 102 or regions to view or scan paths 104 to follow from an exterior global perspective, instead of searching from the interior endoscopic viewpoint. In a preliminary diagnosis for example, the surgeon can target specific diagnostic locations on the model 68 with a joystick or other input device, and the endoscope will then automatically direct its view to these locations. These locations could be predetermined locations of interest to the surgeon identified through a medical imaging technique, or they could be selected interactively. In some cases it might be advantageous to load predetermined locations into memory and have the endoscopic view automatically step through them without the surgeon having to select points on the model 68. Tactile feedback joysticks such as the Phantom Haptic Interface could be used to facilitate the selection of viewing targets on or in the model 68.

Figure 6:
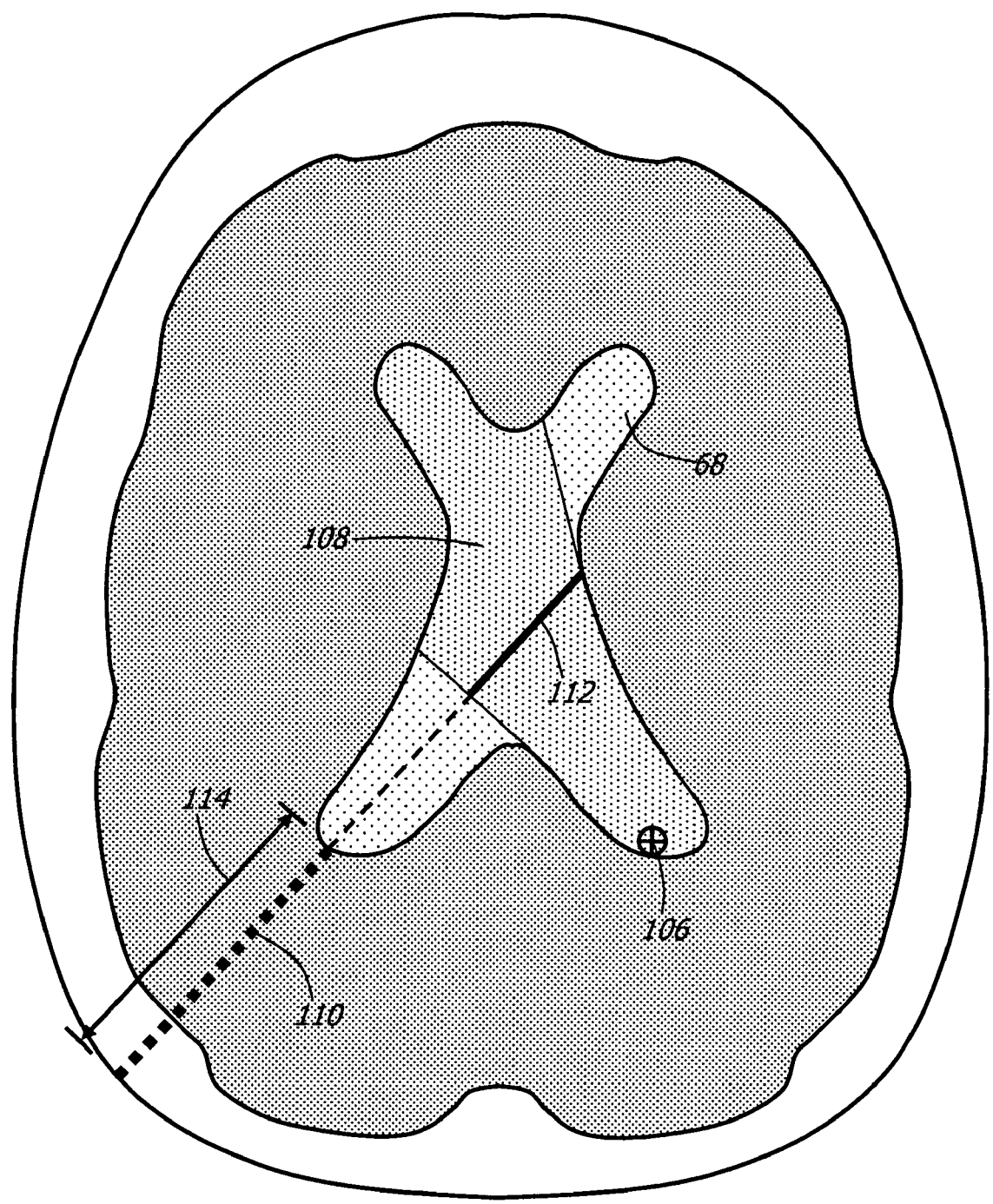
FIG. 6 shows an example of endoscopic surgical approach planning relative to a reconstructed model of a coronal imaging plane according to a method of the present invention.

One of the important features of the present embodiment is its surgical approach planning capability. Because a variable direction of view endoscope can change its line of sight once it is positioned in a cavity, its entry angle can be chosen from a large range. This makes it easier to avoid critical or delicate anatomy when positioning the endoscope. FIG. 6 schematically illustrates surgical approach planning with the present invention. The user can select a target point 106 which has an associated set of points 108. The target point 106 is visible from each point in this set 108. Once the surgeon has selected a target 106, there are three options for the next step: select the endoscope tip location, select an entry corridor or entry line 110, or input the endoscopic field of view. After the user has selected any two of these three options, the central control unit can determine the third. Typically the entry corridor 110 will be selected first because the surgeon's primary concern is to determine the entry path which provides adequate access to the surgical target in the safest way. Once the entry corridor 110 and the target 106 have been determined, the computer can with standard computer graphics and machine vision algorithms compute and display the set of tip locations 112 acceptable for viewing the target 106 for a given endoscope. With fixed viewing endoscopes, the selected entry corridor 110 may not be possible for a given target 106. In such cases the computer could calculate and display the range of acceptable entry corridors for a given endoscope if the user has input its field of view and viewing angle. It is only with omnidirectional scopes that all entry corridors are possible, giving the surgeon complete freedom of selection. The set of tip locations 108 available for a given target 106 will depend on the field of view of the endoscope, the mobility of its view vector, and the shape of the surgical cavity. For example, the set 108 could be limited even for an omnidirectional endoscope because of protruding tissue obstructing the target. However, this set 108 is always much smaller for a fixed angle scope. The computer can also display possible combinations of entry corridors and tip locations for a given target 106 and endoscope type, giving the surgeon the opportunity to evaluate the combination which yields optimal positioning of the endoscope. It is also possible for the computer to suggest favorable entry corridors for a given target 106 based on the endoscope type and anatomical data, making it possible for the user to insert the endoscope along the recommended path and then "look" in the direction of the target 106 upon arrival in the cavity. This type of obstacle avoidance path planning would include a minimal distance feature which calculates and displays a minimal entry distance 114. The approach planner would also graphically display the viewable area associated with each entry tip location on the model 68, giving the user instant feedback as to what she can expect to be able to see from various view points. This includes indicating spots which would be occluded by intervening/overhanging tissue, and spots which would lie in blind zones of the endoscope based on the endoscope's insertion angle and tip position. The type of planning described in this paragraph could also be applied to other types of surgical tools for which the system could calculate and display the set of reachable points for a given tool configuration and entry corridor.

Figure 7:
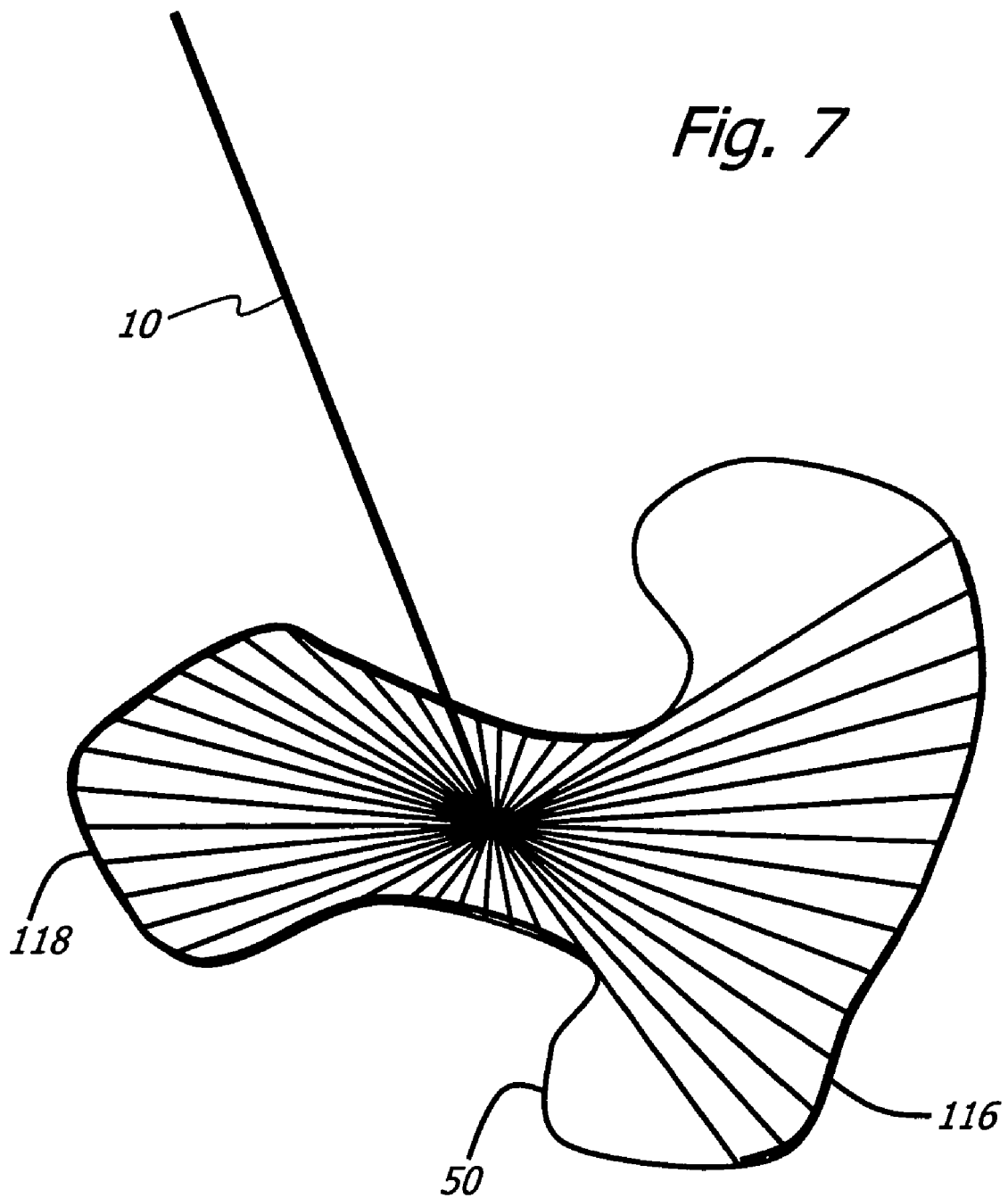
FIG. 7 illustrates a method of enhanced endoscopic positioning by displaying the endoscopic viewable area according to the present invention.

Another valuable diagnostic and surgical planning feature is displaying the subset of points of a scan data set corresponding to the parts of the anatomy which an endoscope is capable of seeing from a given position. This is illustrated in the 2-dimensional example of FIG. 7. Every point on the parietal wall of a cavity 50 to which a straight uninterrupted line of sight can be drawn from a given endoscope tip position is selectively visible with an omnidirectional endoscope. Two boundary point sets 116, 118 show which regions of the parietal wall the endoscope will be able to see from its current position. Based on anatomical scan data of the anatomy, the point sets 116, 118 can readily be established using well known computer graphics algorithms for visible surface determination. These sets 116, 118 are continuously recalculated and displayed as the endoscope tip position changes, giving the user dynamic feedback as to what part of the anatomy can be made visible from the current endoscope position.

The integrated omnidirectional endoscopic image guided stereotactic system can also provide the endoscope itself with safe entry and retraction procedures. One of the biggest advantages of an omnidirectional endoscope is its ability to look forward during insertion, and then change its line of sight once the tip is inside the surgical cavity. Fixed viewing scopes with an off-angle view can be dangerous because they are not "looking" in the direction they are being plunged. This can be likened to driving a car without watching the road. If the omnidirectional endoscope is plunged manually, it can be programmed to do intermediate reconnaissance scans on its way into the cavity. For example, at certain preset depths determined from stereotactic information, the plunging procedure would temporarily stop and allow the endoscope to scan or look in prescribed directions to verify its location and also look for any obstacles in its path. If the endoscope is fully automated, it plunges itself a certain distance before stopping and stepping the surgeon through a predetermined scan. If the scan is satisfactory, the surgeon instructs the endoscope to return to its forward-looking configuration and plunge another incremental distance, and so on. A similar procedure could be performed as the endoscope is retracted.

Figure 8A:
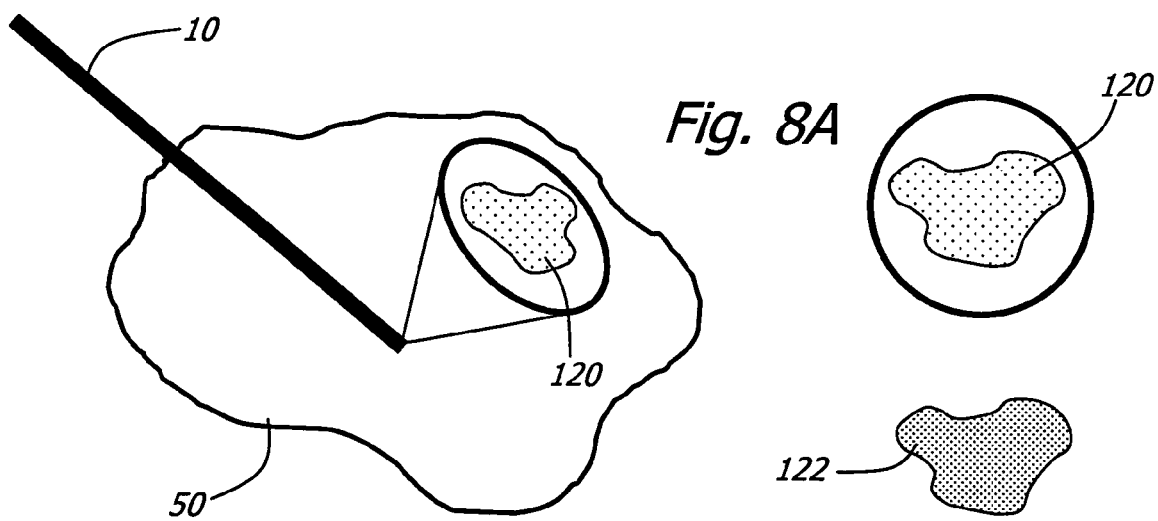
FIGS. 8A, 8B, 8C, and 8D illustrate a method of the present invention of establishing the global position of an endoscope without the need for traditional stereotactic location techniques.
Figure 8B:
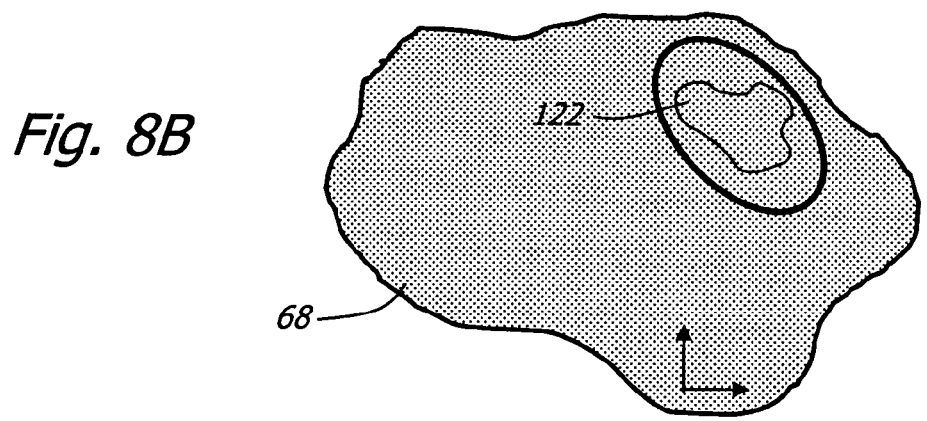
Figure 8C:
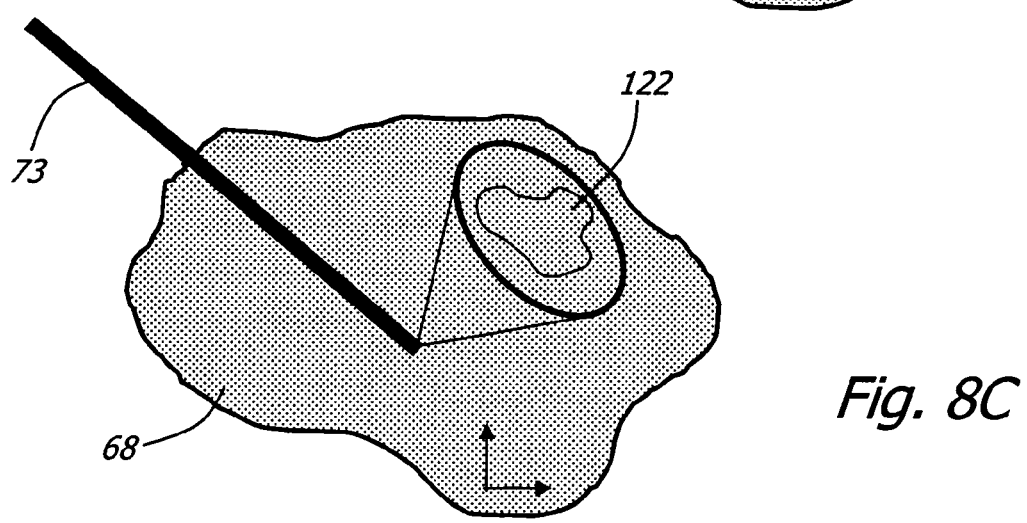
Figure 8D:
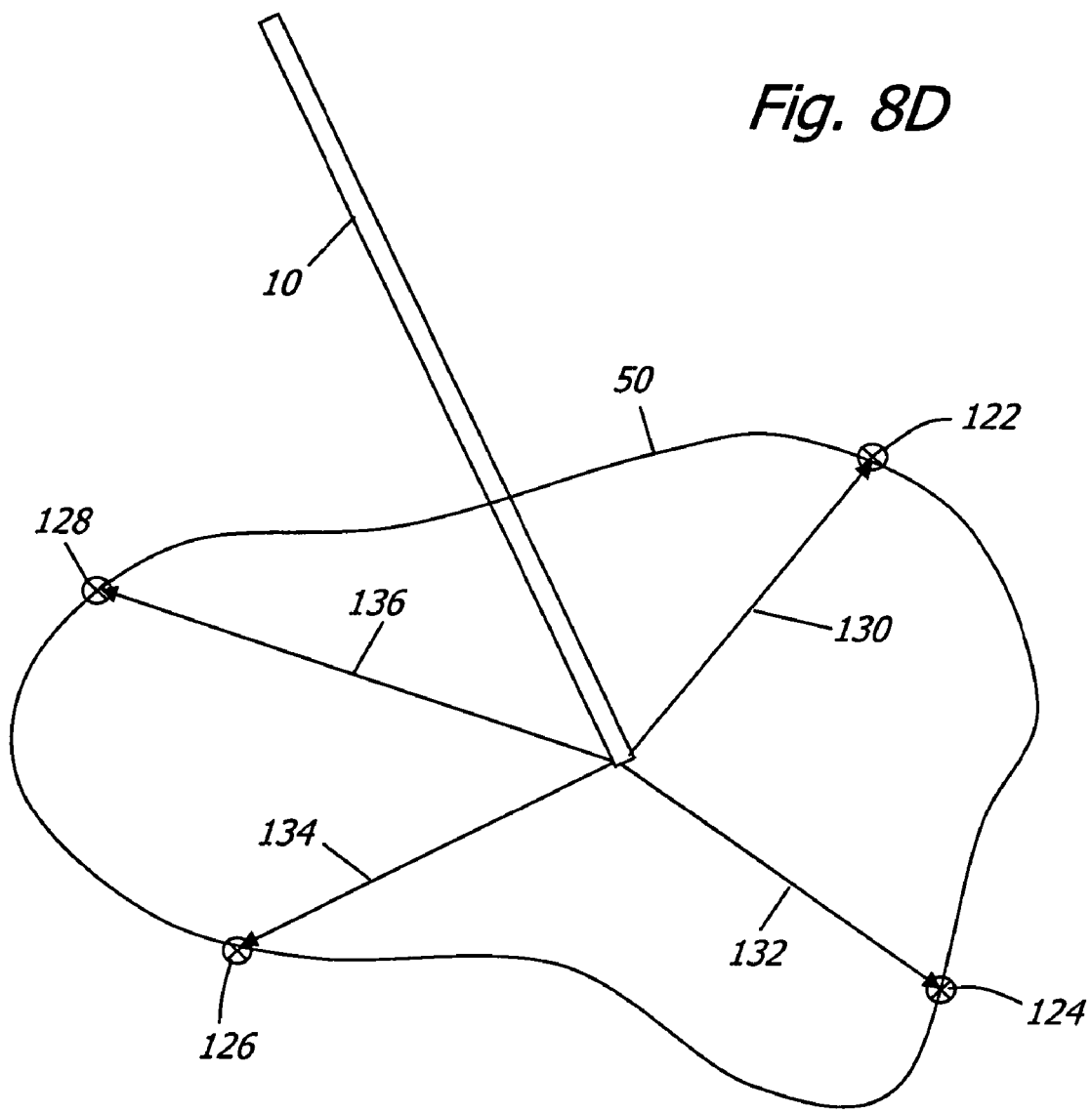

It is possible to establish the global position of an endoscope with respect to a set of volumetric scan data without the use of external sensors, such as the cameras 64 (FIG. 3). This is illustrated in FIGS. 8A, 8B, 8C, and 8D. An endoscope 10 inserted into an anatomical cavity 50 searches for a landmark 120 automatically or controlled by the user. Once a landmark 120 has been located, the image data is matched with a stored electronic representation 122 of the landmark in question. Matching is accomplished by standard pattern matching or machine vision algorithms. Once a satisfactory match has been achieved, the location of the endoscopic view as seen on the reconstructed model 68 of the cavity 50 is known, as illustrated in FIG. 8B. The relative position of the endoscope 10 and the cavity 50 can then be determined from the endoscope configuration data, as shown in FIG. 8C by a graphical representation of the endoscope x and the model 68. For greater accuracy, four landmarks 122, 124, 126, 128 (FIG. 8D) are needed for the endoscope 10 to establish its global position. By matching four landmarks on the volumetric model 68 with the actual endoscopic images, the relative endoscope configurations for each of the four viewing directions 130, 132, 134, and 136 can be used to compute the spatial position of the endoscope 10 relative to the anatomy 50. Fewer landmarks are needed in certain cases. More landmarks provide increasingly better position accuracy. In this way the endoscope effectively locates itself in a surgical environment by collecting local visual information that can be correlated with preexisting data about the surroundings, much like a person would orient herself in a city by identifying known buildings or landmarks. Thus, a global perspective of the endoscope can be constructed entirely without external sensors or instrumentation.

Accordingly, the present invention provides new endoscopic and surgical orientation capabilities, global monitoring of the endoscopic position and viewing direction, and improved surgical approach and procedure planning.

The present invention has been described above in terms of a presently preferred embodiment so that an understanding of the present invention can be conveyed. However, there are many configurations for a variable direction-of-view endoscope and method for viewing not specifically described herein but with which the present invention is applicable. Many structural and material variations are possible, as are variations in application. For example, while the examples were given with respect to an endoscope for use in surgical procedures, the present invention would be equally applicable with respect to a borescope for use within various mechanical structures, or for other types of variable direction probes which use wave lengths other than visible light. The scope of the present invention should therefore not be limited by the embodiments illustrated, but rather it should be understood that the present invention has wide applicability with respect to viewing or sensing instruments and procedures generally. All modifications, variations, or equivalent elements and implementations that are within the scope of the appended claims should therefore be considered within the scope of the invention.

We claim:

1. A method for improving a diagnostic or surgical procedure involving a variable direction of view endoscope with a variable line of sight comprising:
   acquiring volumetric scan data of a subsurface structure;
   positioning said endoscope relative to said subsurface structure;
   acquiring internal endoscope configuration data;
   establishing the position of said endoscope relative to said subsurface structure; and
   based on said volumetric scan data, said endoscope position data, and said internal endoscope configuration data, displaying a graphical model of said subsurface structure reconstructed from said volumetric scan data, a graphical representation of said endoscope relative to said subsurface structure, and a graphical representation of said endoscopic line of sight relative to said subsurface structure and said endoscope;
   selecting a target point relative to said volumetric scan data;
   instructing said endoscope to automatically direct its line of sight towards said target point: and
   updating the display of the relative positions of said endoscope and endoscopic line of sight relative to said graphical model of said subsurface structure as the endoscope automatically directs its line of sight towards said target point.

2. The method of claim 1, further comprising:
   displaying a representation of the rotational orientation of the endoscopic view.

3. The method of claim 1, wherein said establishing endoscope position relative to said subsurface structure comprises:
   correlating at least one endoscopic view with the corresponding region of said volumetric scan data by feature matching and identification; and
   computing the relative position of said endoscope and said subsurface structure using said internal endoscope configuration data for each said endoscopic view and the location of each said corresponding region obtained through said feature matching, and identification.

4. The method of claim 1, further comprising:
   selecting a path relative to said volumetric scan data; and
   instructing said endoscope to direct its line of sight to follow said path.

5. The method of claim 1, wherein said endoscope includes a transponder tracked by a camera.

6. The method of claim 5, wherein the transponder is an LED.

7. The method of claim 1, wherein the establishing of the position of said endoscope includes using features on a patient's body.

8. The method of claim 1, wherein the establishing of the position of said endoscope includes using fiducial markers on a patient's body.

9. the method of claim 1, wherein the position established is saved as a memory position.

10. The method of claim 1, wherein said representations further include a representation of an endoscopic view cone.

* * * * *